United States Patent [19]

Seale

[11] Patent Number: 5,635,784
[45] Date of Patent: Jun. 3, 1997

[54] BEARINGLESS ULTRASOUND-SWEEP ROTOR

[76] Inventor: Joseph B. Seale, 36 Ledge La., Gorham, Me. 04038-1208

[21] Appl. No.: 387,191

[22] Filed: Feb. 13, 1995

[51] Int. Cl.$^6$ .................... H02K 7/09; A61B 8/12
[52] U.S. Cl. .................... 310/90.5; 310/40 MM; 128/662.06
[58] Field of Search ............... 310/90.5, 128, 310/40 MM; 128/662.06, 666, 663.01, 662.03

[56] References Cited

U.S. PATENT DOCUMENTS

| | | | |
|---|---|---|---|
| 4,025,166 | 5/1977 | Felstead | 359/305 |
| 4,977,898 | 12/1990 | Schwarzschild | 128/662.06 |
| 5,115,814 | 5/1992 | Griffith | 128/662.06 |
| 5,240,003 | 8/1993 | Lancee | 128/662.06 X |
| 5,271,402 | 12/1993 | Yeung | 128/662.06 X |
| 5,282,472 | 2/1994 | Companion et al. | 128/662.06 |
| 5,294,854 | 3/1994 | Trumper | 310/90.5 |
| 5,313,950 | 5/1994 | Ishikawa | 128/662.06 |
| 5,345,127 | 9/1994 | New | 310/90.5 |
| 5,543,673 | 8/1996 | Katsumata et al. | 310/90.5 |

*Primary Examiner*—Steven L. Stephan
*Assistant Examiner*—Judson H. Jones
*Attorney, Agent, or Firm*—Chris A. Caseiro; Thomas L. Bohan

[57] ABSTRACT

An ultrasonic imaging device including a bearingless levitating rotor for rotating a reflective mirror. The device may be used to image from within a hollow object and is particularly suited for use in intravascular imaging. The levitation of the rotor is achieved by forming the rotor as a permanent magnet structure having three distinct magnet regions, two having opposing dipole moments axial to the rotor orientation and one having a dipole moment transverse to the rotor orientation, the transverse magnetic region lying between the first and third magnetic regions. The rotor is radially centered within a housing using passive magnetic suspension elements, including permanent magnet stators at opposite ends of the housing. The rotor is axially positioned within the housing with an active servo feedback controller. Position-drive and sense coils are used to move and detect the positioning of the rotor. Rotation drive coils operate on the transverse magnetic region to cause the rotor to spin. The combination of the magnetic components and the coil detection, positioning, and rotation mechanism yields an imaging device with a rotor having no direct mechanical linkages.

26 Claims, 2 Drawing Sheets

BEARINGLESS ULTRASOUND-SWEEP ROTOR

BACKGROUND OF THE INVENTION

1. Field of the Invention

The present invention relates to devices for ultrasonic imaging of hollow objects. More particularly, the present invention relates to devices for controlling the positioning and rotation of mirrors used to transmit and receive ultrasonic signals. Still more particularly, the present invention is related to magnetically-operated devices for ultrasonic intravascular imaging. The present invention includes methods and systems for levitating and positioning objects.

2. Description of the Prior Art

The use of ultrasonic imaging systems for evaluating the interior of hollow objects is well known. In the medical field in particular, such devices have been employed for the purpose of examining the condition of a patient. Of necessity, such devices must be very small and essentially self-contained. For the most part, these devices include a transducer that transmits ultrasonic signals and a receiver that recovers the response signal. The transducer and receiver may be separate components, or they may be incorporated as part of a single crystal.

The devices used in ultrasonic imaging within a hollow object sweep the "beam," or line of sensitivity for transmission and reception, through an arc or circle, either by phased array techniques, or by selection from among multiple transducers differently aimed, or by rotation of a single transducer, or by rotation of a mirror that reflects and sweeps the alignment of a single-transducer beam. The purpose of sweeping is to provide a sectional view into and beyond the walls of the hollow object. Among these sweeping techniques, the phased array approach is the most expensive, difficult to miniaturize, and demanding of multiple connections between electronic and electro-acoustic areas. These multiple connections imply cabling or intimate integration of active semiconductor devices with metalizations driving and sensing separate regions of a transducer with differing phase responses. It is impractical, in a very small intravascular transducer, to provide many broadband transmission lines, low in crosstalk, within a cable, and it is similarly impractical to shrink an integrated semiconductor-transducer device to the needed size. Selection from among multiple transducers entails cabling problems and severe constraints on the size of individual transducers, implying problems with directional focusing and sensitivity. Single-transducer approaches offer the best possibilities for a transducer of maximum size and aperture, to achieve high sensitivity and directionality, within a constrained overall package size. Among these approaches, the rotatable mirror avoids the problems of commutation of the ultrasound electric signal from circuitry to the rotating transducer.

A well-explored approach with a single transducer is the "speedometer cable" configuration, locating a transducer or mirror at the distal end of a cable that rotates inside the lumen of a catheter. The effectiveness of this approach declines at very small catheter diameters and where the catheter must follow a serpentine path through human vasculature. Under these conditions, a uniform rotation driven at the proximal end results in a very non-uniform rotation at the distal "business" end as the cable binds, becomes twisted, and then slips to give a sudden angular whip. Thus, it has proved impractical to shrink coronary artery imaging transducers below an outside diameter of 0.040", and even on that scale, performance is limited.

Rotation drive by a micromotor has been explored using electric and hydraulic means. In the hydraulic motor approach, a rotary impeller is driven by fluid flow through the catheter, typically rotating an ultrasound mirror, so that electrical commutation of the transducer signal is avoided. To obtain consistent indication of the angular alignment of the mirror, it is necessary to provide a rotation encoder, which adds expense and difficulty in miniaturization. In the electric motor approach, a physical constraint is electromechanical efficiency, which inherently declines as a function of physical dimensions, commonly falling below 1% on the scale of a coronary artery device. On this scale, even a small bearing friction stops rotation or demands a power input sufficient to burn up the motor. The extremely low rotational inertia of a micromotor implies that angular momentum does not smooth out rotation, so that very small bearing nonuniformities result in jerky rotation. A small particle of dust will jam a bearing. As a result of these difficulties of small scale, even expensive tooling and techniques for maintaining extremely tight geometric tolerances have proved inadequate.

While magnetic levitation approaches may have been considered by researchers in an attempt to overcome the bearing friction and geometric tolerance problems of micromotors, it might appear that the physics dictating declining electromechanical efficiency with declining scale would preclude magnetic levitation on a very small scale, barring body-temperature superconductors, because such devices would burn up generating the needed levitation forces. It is known from physics that, barring superconductors, the passive interactions of permanent magnets cannot result in simultaneous position stabilization with respect to three orthogonal position axes. It has not been obvious that position-correcting control forces can be used dynamically to correct the position of a micromotor rotor to that unstable and time-varying position, in the force field set up by passive permanent magnet interactions, where the passive forces counterbalance the gravitational and acceleration forces exerted on the rotor. The force perturbations generated by electric currents then serve only to correct transient position errors, along one or two unstable axes, arising from changes in externally-imposed accelerations, from servo transducer noise, and from the inherent passive tendency toward exponential growth of position errors. The forces required to launch a rotor to a levitated position of passive dynamic force balance are then of such short duration that the thermal capacity of magnetic coils safely absorbs the transient energy. The practical implementation of such an approach, leading to a simple mechanical and electronic design with forgiving tolerances and low tooling and fabrication costs, is a needed breakthrough for intravascular imaging, as realized in the invention to be described herein.

SUMMARY OF THE INVENTION

In order to avoid the problems associated with prior imaging systems, we describe a bearingless, electromagnetically levitated rotor, one end of which is an oblique ultrasound mirror used to reflect the beam of sensitivity of a fixed, axially-aligned ultrasound transducer into a swept radial plane or cone, depending on the angle of the mirror. The purpose of the levitation is to avoid mechanical bearings and allow for rotation with very low friction, such that rotation can be achieved even with the extremely low torques achievable on the miniature scale needed, e.g., for imaging from within the lumen of a coronary artery. A further goal of the design is extreme simplicity of the stator/rotor assembly, both to facilitate miniaturization and to lower the cost to a range where a disposable assembly is practical.

The cross-sectional schematic at the top of FIG. 3 will assist in visualization, though the text description immediately below is intentionally more general than the particulars of the figures, which are discussed in the Preferred Embodiment section. The rotor consists of a symmetric permanent magnet structure made physically (but not magnetically) asymmetric by the addition of the oblique ultrasound mirror on one end. The magnet structure is conceived as three separate magnets, though it may be manufactured as a monolithic cylinder of magnetic material, magnetized non-uniformly to achieve the effect described below in terms of three separate magnets or magnetic regions. There are two end magnets, poled axially and oppositely, and a center magnet, which is a "cross-axis" magnet poled at right angles to the rotor axis. This cross-axis magnet can be a physical cylinder whose geometric axis is aligned to the rotor axis, but which is poled in a direction perpendicular to the geometric axis. If the end magnets are axially poled cylinders, then the three rotor magnets can be configured to abut, flat-end to flat-end, forming a single cylinder with flat ends. The oblique mirror may be conceived as a cylinder cut square on the end that abuts the rotor magnet cylinder, and cut obliquely on the other flat face, e.g., at 45 degrees to the cylinder axis. When this mirror is joined to the rotor magnet cylinder, the oblique reflecting surface faces outward. The diameter of the cylinder into which the oblique mirror is cut may exceed the diameter of the magnetic section of the rotor, and an extension of the non-magnetic mirror material to the magnetic section at a reduced diameter may be employed to make space for coils in a very compact geometry. The stator includes two axially-poled permanent magnets located beyond opposite ends of the rotor along the assembly axis. In a typical design with a magnetically symmetric rotor (i.e. the rotor end magnets having equal but oppositely-directed dipole moments), matching stator magnets are located at equal distances axially beyond either end of the rotor with respect to the center position of the rotor magnet. These stator magnets are oriented oppositely and axially so that each one attracts the end of the rotor nearer to it and repels the farther end. A first objective of the "passive" magnetic suspension components is to align the rotor axially, which is accomplished in two ways: 1) the forces on the end rotor magnets, pulling them apart in an axial direction, tend to align the rotor; and 2) the magnetic field through each rotor magnet generates a torque in that individual magnet, proportional to angular alignment error and directed to correct that error. A second objective of the passive magnetic suspension is to center the rotor against radial offsetting forces, such as gravity. As will be seen, axial centering cannot be achieved passively, simultaneous with passive radial centering, and so active servo feedback is needed for axial centering.

The stator also includes one or two windings, coaxial with the stator permanent magnets, used to accomplish servo control of axial position. Specifically, the purpose of this winding or windings is 1) to push the rotor axially under control, and 2) to detect the axial velocity of the rotor via the induced coil voltage. In a typical two-coil configuration, one coil at one end of the rotor acts as the axial driver, while the other coil at the other end of the rotor acts as the axial motion detector. A single coil can both drive and detect. In a time-multiplex mode, for example, pulses of current can be applied to drive the rotor and, between pulses, detected voltage from the open-circuit coil indicates rotor velocity. A sufficiently rapid alternation between drive pulses and velocity detection events permits servo control of rotor position. In a simultaneous drive/sense approach, the drive coil becomes a leg of a balanced bridge circuit, wherein velocity-induced voltage is detected as bridge imbalance, independent of the voltages associated with driving the coil. The impedance bridge approach is probably not feasible on an extremely miniaturized scale, where the induced voltage becomes an extremely small fraction of the drive voltage. The time-multiplex approach has potentially greater sensitivity, and the two-coil approach has probably the best feasibility prospects for extreme miniaturization. The stator and rotor together are referred to as the "motor", and the passive and actively-servoed magnetic forces are referred to as the "magnetic bearing", which aligns and centers the rotor in the stator. The rotor would be considered "bearingless" in the conventional mechanical sense.

A fundamental physical principle governing permanent magnet interactions, and thus the dynamics of this motor, is that when a magnetic field sets up a restorative mechanical force on a magnet with respect to a specified spatial direction, then the force field must be negative-restorative or destabilizing with respect to some other spatial direction. In fact, for any set of three mutually perpendicular spatial axes, the sum of positive and negative restorative force coefficients equals zero, summed over the three axes. The rotor described is positively restored, or stabilized, equally with respect to any two perpendicular cross-axis directions. Hence, the rotor must necessarily be negatively restored, or destabilized, with respect to its direction of axial motion. To levitate the rotor, servo-control is applied to axial position, while passive magnetic forces take care of radial centering. In a preferred embodiment of this invention, the servo control is based entirely on detection of the voltage induced in coils by motion of the rotor magnet or magnets. Other approaches to position or velocity detection are feasible but may add complexity to the motor design.

Once levitation has been achieved, the rotor is spun magnetically by the application of a changing cross-axis magnetic field. In a preferred embodiment, multiple cross-axis field coils are driven with properly phased periodic current signals to give a rotating cross-axis field. A three-coil geometry with a three-phase sinusoidal drive is particularly effective at achieving smooth rotation with a strong magnetic coupling.

In the detailed description of the preferred embodiments we shall examine more closely the geometry of the magnets, coils, ultrasound mirror, and ultrasound transducer. Then we shall consider an electronic feedback circuit used to servo the axial rotor position. It will be seen that rotor "position" comes to be defined not geometrically, but in terms of drive coil current needed to maintain a zero velocity signal. "Center position" thus becomes the dynamic position maintained by zero coil current. The geometric location corresponding to electronic center position is found to vary under influences such as gravity. We shall then look more abstractly at the transfer functions arising in the servo loop and see how the loop can be adjusted for stable centering of the rotor. Finally we shall examine the rotation drive mechanism. It is to be noted that the present invention, while directed to the positioning and rotation of a mirror used in ultrasonic imaging, more generally involves a mechanism for levitating and/or positioning an object.

DETAILED DESCRIPTION OF THE PREFERRED EMBODIMENTS

Figure 1:
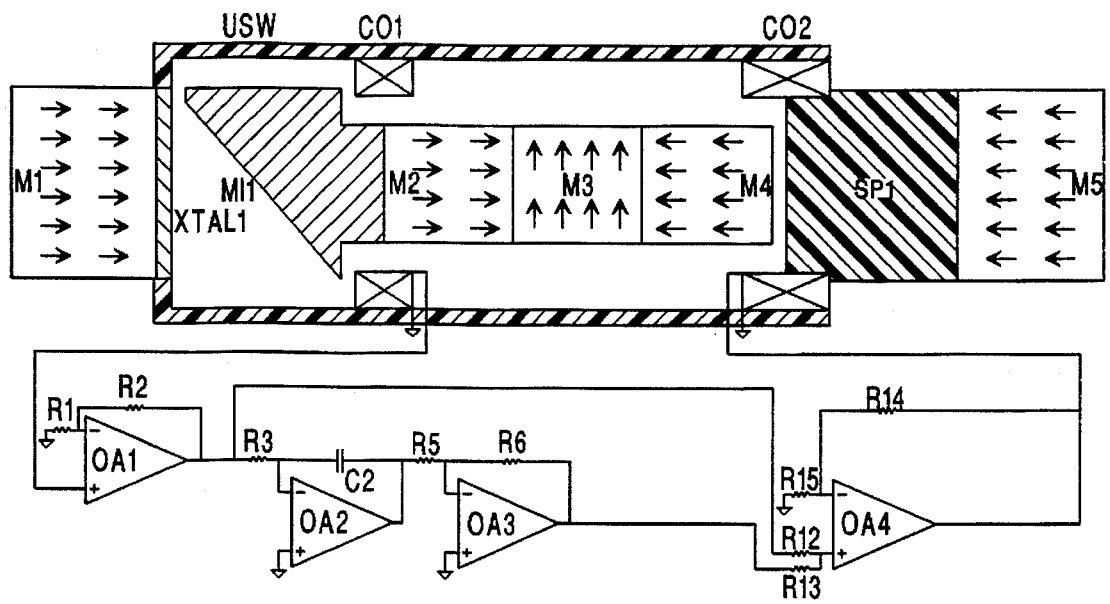
FIG. 1 is a schematic cross-section of the bearingless rotor system of the present invention, with simplified circuitry requiring mechanical initialization and subject to drift.
Figure 2:
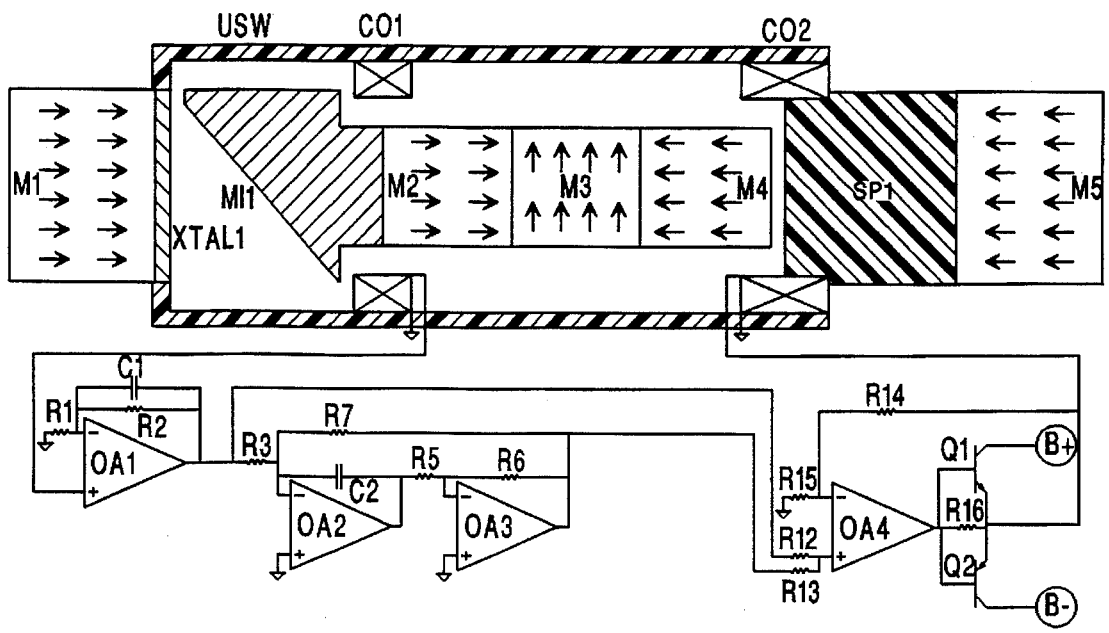
FIG. 2 is a schematic cross-section of the bearingless rotor system of the present invention, with circuitry for correcting initialization and drift errors.
Figure 3:
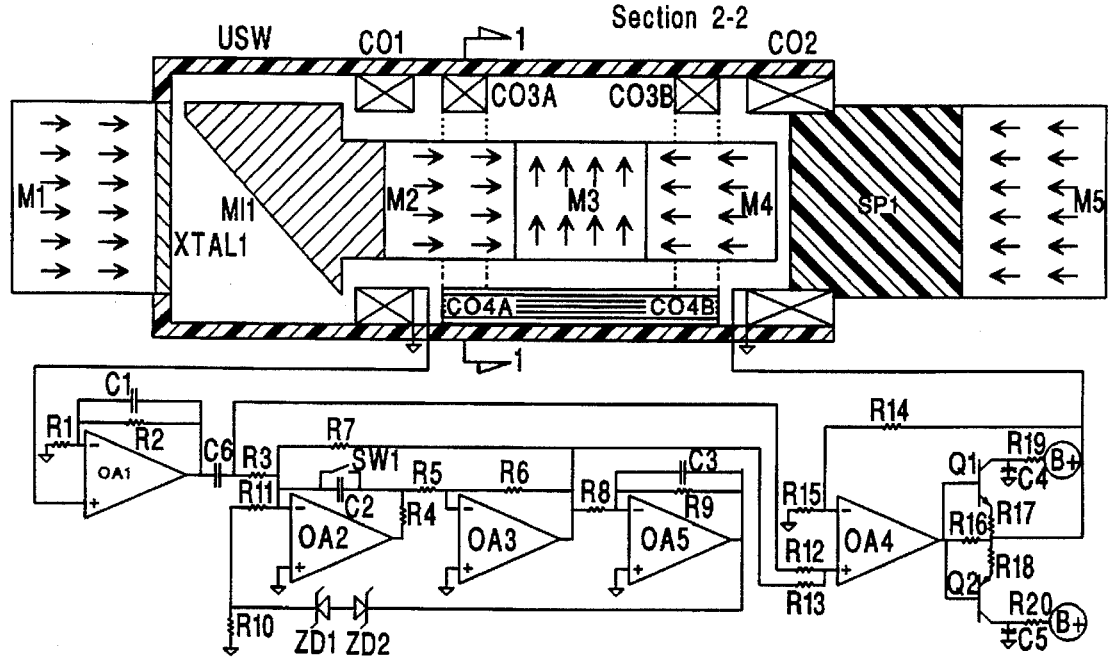
FIG. 3 is a schematic cross-section of the bearingless rotor of the present invention, showing rotation drive coils and fully self-initializing circuitry.

The system for magnetic levitation of a rotor is described in progressive levels of detail with reference to FIG. 1, then FIG. 2, and finally FIG. 3. The mechanical and magnetic assembly is indicated in schematic cross-section, repeated across the top of each of FIGS. 1, 2, and 3, as the circuit schematic below the cross-section schematic is modified toward working form going from figure to figure. The location of one rotation drive coil is indicated in the section of FIG. 3, with a different section in FIG. 4 revealing all three coils for a three-phase rotation drive.

Referring to FIG. 1, a fixed ultrasound crystal, XTAL1, is directed at oblique mirror MI1, which forms one end of the rotor and spins about an axis lying in the plane of the diagram from left to right. The spinning of the rotor and mirror causes the ultrasound beam to sweep a planar or conical field, planar in the case that MI1 is oriented at 45 degrees to the axis of rotation. A cylindrical ultrasound-transmitting window USW enclosing the rotor assembly has an inside diameter to fit over the outside diameter of coils CO1 and CO2, which lie over the ends of the magnetic section of the rotor. The stator structure and ultrasound window capture the rotor in an ultrasound-transmitting fluid. A slightly conical scan path, with MI1 oriented a few degrees away from 45 degrees, may be preferred for reducing the effect of reflections reverberating between the crystal, the mirror, and the cylindrical ultrasound window. FIG. 1 shows the rotor flattened slightly toward a plane perpendicular to the rotor axis. The outer tip of the rotor is also drawn blunted, which provides a surface rather than an edge on which the rotor can land toward the mirror end. Poling orientations of the permanent magnets are indicated by multiple arrows. The magnetically-matched outer magnets of the rotor, M2 and M4, are poled in opposing directions paralleling the rotor axis. The center magnet of the rotor, M3, is poled perpendicular to the rotation axis and is used for coupling magnetic torque to spin the rotor, as will be explained after this current discussion of levitation bearing functions. In the stator assembly, permanent magnet M1 is oriented parallel to the rotor axis and in the same poling alignment as M2, the nearer of the rotor end magnets. Thus, M1 attracts M2 and, much more weakly, repels the more distant M4. At the opposite end of the stator, on the far side of the rotor from M1, M5 is oriented oppositely to M1, so that it attracts neighboring M4 and, much more weakly, repels M2. The fields of stator magnets M1 and M5 roughly cancel at magnet M3. The net effect of the stator magnet fields is to align the rotor to its intended axis, to center the rotor against cross-axis influences such as gravity and accelerations of the entire assembly, and to create a destabilizing or negative restoration of rotor position, with the unstable axial equilibrium position of the rotor being roughly the centered position, midway between the axial motion stops where MI1 bumps the ultrasound XTAL1 and where M4 bumps SP1, a passive spacer extending from the center of CO2 to define the setback of M5 from the rotor.

In FIGS. 1, 2, and 3, coil CO1 on the mirror end is used for velocity sensing while CO2 on the opposite end is used for driving. CO2 is drawn somewhat longer than CO1, where its length beyond the right side of the rotor imposes no constraint on rotor geometry, unlike CO1, whose length constrains the shape of the mirror section of the rotor for maintaining clearance. The larger CO2 is chosen for driving, and smaller CO1 for sensing, in this preferred embodiment. The larger and/or better-coupled coil should be used for driving, since this choice minimizes the peak power required to pry the rotor free of its locked position at one or the other axial extreme on startup. While the coils may be asymmetric with respect to the rotor magnets (as shown here), the positioning magnets in the stator are preferably symmetric with respect to the rotor magnets. If the positioning magnets were made of unequal size or strength in an effort to achieve more convenient or compact positions, e.g. with M5 occupying the space of passive spacer SP1, then problems could arise with rotor alignment. Specifically, the axial gradients of the magnetic fields of the positioning magnets determine the axial forces exerted on M2 and M4. If unequal positioning magnets were placed at unequal distances from the center of the rotor magnet assembly to achieve balanced forces, i.e. balanced field gradients, then the net field strength in the middle of the rotor magnet assembly, at M3, would generally be non-zero. An uncancelled axial field strength at M3 results in a torque exerted on M3 that tends to bring the rotor out of axial alignment. For a rotor spinning fast enough, such a torque causes no significant net misalignment of the rotor axis, but for startup, the rotor could remain misaligned and jammed, unable to start rotation. Hence, a symmetric permanent magnet configuration is the simplest to make work.

Suppose that CO2 carries a drive current in the direction that causes the field to CO2 to reinforce the permanent field of M5. By convention, we will call this a positive drive current, which will strengthen the attraction of M5 on M4 and cause the rotor to accelerate to the right, as illustrated. Similarly, a negative drive current will oppose the field of M5, weaken the attraction of M4, and drive the rotor to the left. When the rotor is moving with a velocity to the right, M2 will be moving away from CO1. Suppose that CO1 is wound with the same spiraling rotation sense as CO2 and connected similarly, e.g., electrical ground to the outside of the winding and the signal lead off the center of the winding as illustrated, except with CO1 turned around axially relative to CO2 just as M1 is turned axially to oppose the poling of M5. Then we see that the field from M2 seen in CO1 is similar to the field of M4 seen in CO2. A positive voltage applied to the signal lead of CO2 causes a positive current flow, a motion of M4 toward CO2, a strengthening of the field of M4 linking the turns of CO2, and a "back EMF" or induced voltage in CO2 that must, by conservation of energy, oppose the positive current flow that gave rise to the motion of M4. Magnet M2 is to the signal-lead current in CO1 as M4 is to the signal-lead current in CO2. If M2 is moving toward CO1, the induced EMF opposes a positive flow of current into the signal lead of CO1, meaning that the induced voltage appearing on the signal lead of CO1 is positive when M2 moves toward CO1. Now a positive signal (voltage and current) applied to CO2 causes M4 to move toward CO2, which in turn causes M2 to move away from CO1, which in turn induces a negative voltage on the signal lead of CO1. Suppose that this negative induced voltage on CO1 is amplified and applied to the signal lead of CO2. The resulting current flow will generate a force that opposes the axial rotor motion, damping that motion.

Such an active damping feedback loop is shown in the electronic schematic below the motor diagram of FIG. 1. The signal lead from CO1 connects to the input of non-inverting amplifier OA1, using feedback resistor R2 to the inverting input and R1 from the inverting input to ground as gain-setting elements. The output signal from OA1 travels by two paths, the upper path being the damping path just mentioned, leading via R12 to non-inverting amplifier OA4, whose output is applied to the signal lead of CO2. Feedback resistor R14 to the inverting input of OA4 and R15 from that input to ground set the gain of OA4.

To stop the motion of the rotor, one needs a stabilizing servo-generated spring coefficient in addition to velocity damping. To achieve this, the velocity-indicating output of OA1 is applied, via current-scaling resistor R3, to the input of inverting integrator op amp OA2, whose feedback capacitor C2 to the inverting input and junction with R3 completes the determination of the integration time constant. Inverting amplifier OA3, with gain regulated by input resistor R5 and feedback resistor R6, inverts the output of integrator OA2, resulting in a non-inverted integral output. This integral of the velocity-induced voltage signal from CO1 changes in direct proportion to change in rotor position. This position signal is summed, via R13 into non-inverting OA4, with the velocity signal arriving via R12, yielding a weighted sum of position and velocity. This weighted sum voltage drives current through CO2. For the typical geometries, coil resistances, and bandwidths of axial rotor motion encountered with small levitation-bearing motors, the inductive voltage of CO2 is substantially smaller than the resistive voltage, so that both electrical current and mechanical force are nearly proportional to the voltage drive signal to CO2, with negligible phase lag. Hence, the electronic loop of FIG. 1 implements a servo-damper and servo-spring that, in combination, can overcome the negative restoration of the rotor and bring the rotor to a stop at some fixed position.

It is readily seen that the fixed position achieved by the circuit of FIG. 1 is not necessarily center position, but depends on the initial integrator output voltage and the initial rotor position. The equilibrium rotor position defined by the feedback loop may be off-center, or even outside the available range of rotor travel. Furthermore, the output of driver amplifier OA4 is likely to be a large, non-diminishing signal that could potentially overheat and destroy drive coil CO2. Even if the system of FIG. 1 is initialized to place the rotor at rest and centered, offset voltages and currents in the circuit will cause the integrator output to drift, so that the rotor will drift from center position and eventually hit a stop. The issues of drift and unzeroed sustained drive current are addressed by the circuit modifications to FIG. 1 appearing in FIG. 2.

Suppose that the rotor is successfully levitated, away from its limit stops but off-center. If the rotor is to the right of its unstable equilibrium position, then it must be pushed steadily to the left to maintain position, so the output from OA4 must be a steady negative signal (by the sign conventions given above). If one wants to know rotor position, one need only look at the servoed voltage on OA4 and know the proportionality coefficient between that voltage and rotor position. A position offset to the right implies a positive output from OA4, which in turn implies a positive output from OA3, the non-inverting integrator output derived from the inverted integral at the OA2 output. Suppose that some component of the OA3 output is fed back to integrating amp OA2 saying, in effect, "If I have to push steadily to the left to hold constant rotor position, then I am going to push a little harder to the left to bring the rotor closer to center and subsequently lessen the effort required." This progressive "extra push" is implemented via feedback resistor R7 (FIG. 2) from the output of inverter OA3 to the input of integrator OA2. Notice that this feedback is regenerative in polarity, the equivalent of negative damping of the electronic circuit. Net positive damping and stability arise when the servo loop is closed through the levitated rotor. This extra feedback signal, superimposed on the spring-damper servo loop, progressively rebiases the center position of the servo spring acting on the rotor, pushing the rotor to the unstable equilibrium position where zero steady drive current is required in CO2.

The geometric position corresponding to this servo-center position will vary, e.g., with gravitational orientation. If the rotor is geometrically centered between its axial stops when lying horizontally, then the rotor will come to rest axially off-center when reoriented vertically. Which way off-center? Up. The rotor will come to rest above center, closer to the upper stator magnet and farther from the lower one, so that the greater attraction of the upper stator magnet compared to the lower one is just enough to overcome the steady downward force of gravity. The rotor exhibits negative axial "sag" with respect to gravity, doing the opposite of what it would do with an ordinary spring. Radial "sag" is positive, i.e. downward from center-axis with the pull of gravity, as determined by the passive magnetic restorative spring for radial offset. The magnitude of positive radial sag along either of two orthogonal radial axes is double the magnitude of negative axial sag, since sag with respect to three orthogonal directions and a given force magnitude must sum to zero.

The circuit of FIG. 2 shows the addition of capacitor C1 in the feedback path of velocity signal amplifier OA1, with C1 paralleling R2. At high frequencies, typically beyond the bandwidth of substantial rotor motion, signal is coupled from CO2 to CO1 by mutual inductance of the coils, independent of rotor motion. This inductive coupling gain, given a large amplification factor by OA1 and sent around the feedback loop, can throw the entire servo loop into high frequency oscillation. C1 serves to limit high frequency loop gain and restore stability.

The circuit of FIG. 2 also shows a complementary PNP-NPN emitter follower output stage boosting the current capability of OA4, consisting of a direct feedthrough current path via R16 from op amp output to final output, a positive-signal emitter follower output path from OA4 via the base of NPN transistor Q1 to final output, and a negative-signal emitter follower output path from OA4 via the base of PNP transistor Q2 to the final output. The collector of Q1 is tied to positive supply "B+" and the collector of Q2 is tied to negative supply "B−". This output current booster permits OA4 to be an ordinary op amp section. Given a reasonably fast op amp, the dynamic crossover distortion associated with this emitter follower topology has no practical effect on the operation of this servo loop.

If the circuit of FIG. 2 is turned on with the rotor lying initially against an axial limit stop, one of two things will happen, depending on the initial offset going into the integrator of OA2. The feedback loop via R7 around OA2 is regenerative, promoting exponential runaway in a direction determined by initial offset or by noise polarity at a critical startup moment. If the runaway is in the "right" direction, the increasing signal to CO2 will pry the rotor away from its limit stop, resulting in a velocity signal returning via OA1. This velocity signal will oppose the open-servo-loop runaway tendency of OA2 via R7, causing the entire electromechanical system to settle, given appropriate dynamic coefficients. If, however, the runaway is in the "wrong"

direction, the rotor will be pushed with increasing force against its limit stop until the electronics overload, leading to a latchup condition. Such a latchup is overcome by the circuit of FIG. 3.

The conspicuous addition in FIG. 3 is the negative feedback path via OA5 and opposing zener diodes ZD1 and ZD2. With input resistor R8 and parallel feedback resistor and capacitor R9 and C3 to the inverting input, OA5 implements an inverting single-pole lowpass filter. If the output at OA3 settles quickly to a small value, the lowpass output from OA5 will never exceed the zener diode thresholds, positive or negative, and OA5 will have no effect on operation. In a latchup mode, however, the large unipolar output from OA3 will quickly drive the OA5 output above the zener threshold, causing a current flow into the inverting input of OA2 via R11. R15 to ground from the junction of R11 and zener diode ZD1 serves to shunt away small zener leakage currents below the sharp zener threshold, improving zener performance, where the impedance magnitude of R11 in a practical design tends to be too high for good performance with series zeners. The effect of the OA5 feedback loop, with a large central deadband, is to reverse any momentary latchup of OA2 and send the drive output in the opposite direction, reversing a temporary latchup condition. If the rotor is stuck or otherwise fails to respond, the loop through OA2, OA3, and OA5 will sustain blocking oscillations, given proper gains and time constants.

These oscillations could potentially overheat the drive coil and cause damage to the coil or to a patient. Instantaneous and cumulative output current flow are therefore limited. To limit instantaneous current flow, typically to about 150% of the minimum current needed to pry the rotor away from a stop, emitter resistors R17 and R18 included as shown in FIG. 3, may be connected in the circuit. R17 and R18 may be sized so that OA4 will reach its output voltage limit as current through R17 or R18 reaches the desired limiting level. To limit cumulative output energy to CO2 following a few cycles of blocking oscillations, current limit resistors R19 and R20 are set in the collector paths of transistors Q1 and Q2, with charge storage capacitors C4 and C5 holding just enough charge to permit a small number of output blocking oscillations at near-full power before the output current limit is reined in substantially by R19 and R20.

In FIG. 3, resistor R4 is added in series with the output of OA2, limiting the peak output signal that can reach R5 going into OA3 and that can reach C2 feeding back to the summing junction of OA2. The design typically calls for making R5 much smaller than R3 (which scales the current magnitude via C2), so that the load on OA2's output via R4 is dominated by R5. Thus, R4 causes the integrator output at the junction of R5 and C2 to clip at a lower level than the op amp voltage limit, which quickens latchup recovery and lessens overshoot. Computer simulations of this circuitry indicate a need for proportioned clipping levels at critical circuit stages to permit recovery from blocking oscillations to a stable equilibrium. If the OA2 integrator output can build up its output magnitude to many times the level that puts the OA4 circuit into current limiting, then OA2's recovery is too slow and the rotor overshoots, latching against alternate stops in a blocking oscillation until C4 and C5 are pulled down and the circuit continues to oscillate without moving the rotor. The circuit has a limited envelope of stable gains, time-constants, deadband thresholds, and limit thresholds. Outside that envelope, permanent latchup or sustained blocking oscillations ensue.

Next, consider switch SW1, which may be closed to short the integration capacitor C2 and initialize the integrator output to zero. If power is initially applied to the circuit with SW1 open, it is likely that OA4 will develop a large output signal before capacitors C4 and C5 have had time to charge fully. The result can be the output of a limiting drive current insufficient to pry the rotor loose but sufficient to keep down the voltages on C4 and C5. This condition results in sustained blocking oscillations in the loop of OA2, OA3, and OA5, without prying the rotor loose. SW1 is therefore closed during power-up and then opened after C4 and C5 have approached full charge. SW1 can be an electronic switch, in which case its operation can be automated. If a disturbance, e.g. the motor falling and hitting a surface, causes the servo circuit to overwork and discharge C4 and C5, setting the circuit into sustained blocking oscillations with the rotor latched, this condition is readily detected by circuitry not shown nor described in detail here, so that SW1 can be closed long enough to re-initialize the circuit. If repeated closures and re-openings of SW1 fail to result in sustained levitation and a cessation of blocking oscillations, then a problem exists and the system should be designed to alert the operator, and possibly to shut down entirely.

The final electronic component added to FIG. 3 is capacitor C6, which blocks DC current flow from the OA1 output to the two signal paths ending in R3 and R12. The net DC gain from CO1 to CO2 via OA1 and OA4 commonly needs to be 1000 or more. Input offset at OA1 is then amplified to a potentially high level, generating an offset in the servoed position of the rotor and giving rise to a sustained high-level signal to CO2, possibly large enough to cause circuit overload or coil overheating or other malfunction. The servo loop can function with a highpass filter inserted (i.e. the C6 coupling), provided that the low-frequency cutoff is low enough. If startup is delayed by closure of SW1 until the charge on C6 approaches equilibrium with the output offset from OA1, then the servo loop can begin and continue operation as if nearly free of offset voltage.

DESIGN GUIDELINES FROM LINEAR DYNAMIC ANALYSIS

The choices of gains and time constants in the circuitry described above are guided by the following transfer function analysis of the servo loop. The axial motion of the rotor itself is described as a simple mass-spring-damper system. Using LaPlace transform notation, with the complex frequency variable "s" in the transform domain representing time differentiation in the time domain, "$s^2$" as second derivative with time, "1/s" as time integral, etc., then we have:

$$s^2 M + sD + K = 0 \qquad 1]$$

for unforced axial motion of a rotor of effective mass M, damping coefficient D, and spring restoration coefficient K.

Coefficient K is negative, representing the destabilizing axial magnetic influence. The magnitude of K can be derived from equations describing the force of attraction between magnetic dipoles as a function of distance. Each magnet in the stator and rotor can be approximated as a point dipole located at the center of the magnet. Given residual B field strength $B_r$ characteristic of the permanent magnet material (e.g., 1.2 Teslas for a high-strength Neodymium Iron Boron magnet), using reversible permeability of the magnetic material MU (which is typically between 5% and 10% greater than free space permeability $MU_0 = 4*pi*10^{-7}$ Webers/Amp-Meter), and using magnet volume VOL (in cubic meters), the dipole moment is roughly MOMENT= $B_r$*VOL/MU. Textbook equations give the axial field strength in terms of dipole moment and distance. The interaction energy between two dipoles (i.e. magnets)

on-axis is the product of the field strength from one dipole measured at the location of the other dipole, multiplied by the dipole moment of that other dipole. Force is the derivative of energy with respect to magnet spacing. From there, with a little textbook help, one derives the negative restoring coefficient K for a geometry such as is illustrated in FIGS. 1, 2, and 3, taking account of the force of each stator magnet on each rotor magnet.

Damping coefficient D arises mostly from the fluid surrounding the rotor. When the rotor moves with axial velocity u, fluid displaced from one end of the rotor must flow through the annular space between the rotor and its container to reach the other end. Approximating the flow as laminar (a sure bet on a microminiature scale) and "steady" i.e. with a nearly equilibrium boundary layer velocity profile at all times (a decent approximation on a microminiature scale and for the frequencies of concern), then one determines the fluid velocity profile v(r) for velocity v at radius r having the form:

$$v = Ar^2 + Br + C \qquad 2]$$

For axial rotor velocity u, the constraints that determine A, B, and C are that v=u at the rotor surface, v=0 at the outer fluid-confining envelope, and the integral of v over the annulus between the boundaries matches the rate of volume displacement past the point of concern, which equals −u times the cross-section area of the rotor. (The flow integral of v opposes the direction of rotor velocity u, as the rotor moves one way and displaced fluid squeezes by in the opposite direction.) If the diameter of the rotor and/or confining envelope differs at different axial locations, as in FIG. 3, then Eq. 2 and subsequent computations are performed at the various diameters to determine an approximate net damping coefficient D. Solving for the radial shear slope dv/dr at the rotor boundary where v=u, multiply that dv/dr by the absolute viscosity, MU, of the fluid to obtain shear stress, then multiply that stress by the affected rotor surface area to determine shear force associated with u at the specified inside and outside radius and axial length. Repeat this calculation for the various radii associated with different portions of the rotor length and sum the computed shear forces to get a net damping force. Dividing this net force by u gives the damping coefficient D.

Mass coefficient M includes two components: $M_r$, the actual rotor mass, and $M_f$, the mass attributed to inertia of entrained fluid, which can be a significant fraction of $M_r$. To compute $M_f$, use Eq. 3, relating mass to kinetic energy:

$$M_f = 2 * E_k / u^2 \qquad 3]$$

To compute fluid kinetic energy, use the distribution of velocity v from Eq. 2, determine fluid kinetic energy density=RHO*$v^2$/2 for fluid density RHO, and integrate this energy density over the annular volume surrounding the rotor to obtain $E_k$. Since velocity v is proportional to u, one can express $E_k$ in terms of $u^2$ rather than $v^2$. Then dividing through $E_k$ by $u^2$ and multiplying by 2 yields effective fluid mass $M_f$ of Eq. 3. Summing this with $M_r$ yields total mass M for Eq. 1.

When the rotor is subject to electromagnetic servo control, Eq. 1 is modified to include the servo loop. The important electromechanical coupling coefficient is named "TM" after its units, Tesla-Meters. Converting units, it is readily shown that:

Tesla-Meters=Newtons/Ampere=Volts/(Meter/Second)

The Newtons/Ampere units indicate a ratio of force to electric current, while the Volts/(Meter/Second) units indicate a ratio of voltage to velocity. For a sense coil whose open-circuit voltage is taken as a measure of velocity, the Volts/(Meter/Second) units are relevant. For a drive coil whose applied electric current generates a force, the Newtons/Ampere units are relevant.

The simplest way to approximate TM for a coil at an axial distance x from a permanent magnet is to use the textbook equation for the on-axis field strength of a current-carrying wire loop, and (e.g., on a computer) sum the contribution from each turn of the coil to the field at the center of a rotor magnet, as a function of coil current I. Multiplying this field strength by magnet dipole moment yields magnetic energy. Computing the derivative of this energy with respect to change in axial magnet position x yields the magnetic force, per ampere of I, between the coil and the magnet. This yields coefficient TM in Newtons/Ampere, which for a sense coil is numerically identical to the Volts/(Meter/Second) sensitivity to detect velocity. (As a consistency check, one can use the dipole field equations to compute off-axis radial B-field Teslas from the permanent magnet at each turn of the coil and integrate over Meters of winding length to obtain a result in Tesla-Meters, which should have the same value as the Newtons/Ampere figure.)

Let $TM_s$ be the coupling coefficient for the sense coil, and $TM_d$ be the coupling coefficient for the drive coil. Looking at the servo loop of FIG. 1, let G be the net DC voltage Gain from the sense coil to the drive coil, and let $R_d$ be the ohmic resistance of the drive coil. Then define an effective "loop resistance" R:

$$R = R_d / G \qquad 4]$$

This R gives the ratio of sense-coil volts to drive-coil amps, given the actual drive coil resistance and the voltage gain. We see that sensed voltage $V_s$ is given by $TM_s$ multiplied by velocity u:

$$V_s = TM_s * u \qquad 5]$$

Drive current $I_d$ is then expressed in terms of R:

$$I_d = V_s / R \qquad 6]$$

Drive force $F_d$ is drive current times coupling coefficient $TM_d$:

$$F_d = I_d * TM_d \qquad 7]$$

Combining all these equations yields the ratio of drive force to velocity:

$$F_d / u = D_{em} = TM_s * TM_d / R \qquad 8]$$

We have named this force/velocity ratio $D_{em}$, the electromechanical damping factor of the servo loop. If we take the voltage signal going from sense coil to drive coil and apply some transfer function, e.g. by summing the time-integral of the voltage with the original voltage, then we have effectively multiplied the damping coefficient $D_{em}$ by that transfer function, which we will call H(s). This modified electromechanical "damping" feedback is now included in Eq. 1 to express the characteristics of the servo loop:

$$s^2 M + s(D + D_{em} * H(s)) + K = 0 \qquad 9]$$

In the circuit of FIG. 1, we have:

$$H(s) = 1 + 1/(s*T_1) \text{ (FIG. 1 circuit)} \qquad 10]$$

where $T_1$ is the effective integration time constant of the integrator, taking into account any gain of the integrator output relative to the Direct-Coupled or DC path through the loop (i.e. T1=seconds until the integral voltage signal grows to match the size of the DC signal that is applied to the drive coil). Solving for the transfer function of the FIG. 1 circuit, we have:

$$s^2M + s(D+D_{em}*(1+1/(s*T_1))) + K = 0 \quad 11]$$

$$s^2M + s(D+D_{em}) + (D_{em}/T_1 + K) = 0 \quad 12]$$

We see that the servo loop increases the damping and adds a positive servo-spring restoration to the negative restoration constant K. To stabilize the system, one needs $D_{em}/T_1$ to exceed the magnitude of K by a comfortable margin, but causing $D_{em}/T_1$ to be orders of magnitude larger than K implies an unnecessarily large loop gain and the probability of difficulties in stabilizing the servo loop, given the inevitable band-limit rolloffs and phase shifts not in the accounting of Eq. 12. A natural magnitude for the electromechanical "spring" is to set $D_{em}/T_1 = 2*|K|$, twice the absolute value of K, in which case we have:

$$s^2M + s(D+D_{em}) + |K| = 0 \text{ when } D_{em}/T_1 = 2*|K| \quad 13]$$

A minimum settling time is obtained when this system is critically damped, which occurs when:

$$D + D_{em} = SQRT(M*|K|) \text{ for critical damping} \quad 14]$$

Eq. 14 gives us a method to scale $D_{em}$, which leads to solution for $T_1 = D_{em}/(2*|K|)$ and which determines the basic loop gain G. We have seen, in relation to FIG. 2, that the transfer function H(s) needs to be altered to give a servo loop that seeks a center of balance for the rotor. Specifically, the regenerative feedback path around the OA2 integrator via R7 gives rise to a second time constant, $T_2$, related to $T_1$ by:

$$T_2 = T_1 * (R7/R3) * (R5/R6) \quad 15]$$

Check: if R7 approaches infinity, opening that feedback circuit, then $T_2$ approaches infinity and it takes infinitely long for the R7 feedback path to make any difference. Similarly if R5 goes to infinity or if R6 goes to zero. The transfer function $H_i(s)$ for the OA2 integrator modified by regenerative feedback is given by:

$$H_i(s) = 1/(sT_1 - T_1/T_2) \quad 16]$$

Check: if the regenerative feedback loop is driven to zero influence, e.g. by driving R7 to infinity and thereby driving $T_2$ to infinity, then $H_i(s)$ approaches $1/sT_1$, a simple integrator, which is the second term in Eq. 10, summed with the normalized direct gain of 1 operating in parallel with the integrator. Finding the root of the denominator polynomial gives the pole of the system, which is positive real at s=1/T2, implying an exponential runaway with the time constant of the feedback path, regardless of the input. Clearly this $H_i(s)$ circuit, being unstable, is of no practical use unless closing the servo loop stabilizes this part of the electronics. To resolve this issue, we sum $H_i(s)$ with 1 as in Eq. 10, which adds in the direct-gain path of the servo feedback loop, and proceed to determine the poles of the closed servo loop. In place of H in Eq. 10 we now have H':

$$\begin{aligned} H'(s) &= 1 + 1/(sT_1 - T_1/T_2) \\ &= 1 + (T_2/T_1)/(sT_2 - 1) \\ &= (sT_2 - 1 + T_2/T_1)/(sT_2 - 1) \end{aligned} \quad 17]$$

Our modified Eq. 11 becomes:

$$s^2M + s(D+D_{em}*(sT_2 - 1 + T_2/T_1)/(sT_2 - 1)) + K = 0 \quad 18]$$

Multiplying through by $(sT_2-1)$ and collecting terms yields a third order characteristic polynomial:

$$s^3(T_2M) + s^2(T_2(D+D_{em}) - M) + s(D_{em}(T_2/T_1 - 1) - D + T_2K) - K = 0 \quad 19]$$

Moving toward a normalized polynomial, we divide through by $T_2M$:

$$s^3 + s^2((D+D_{em})/M - 1/T_2) + s((D_{em}/M)(1/T_1 - 1/T_2) - D/T_2M + K/M) - K/MT_2 = 0 \quad 20]$$

Since K is negative, the K/M term multiplied by s is negative, and the constant term $-K/MT_2$ is positive. For a stable system, all the roots of polynomial 20 must have negative real parts, which cannot happen if any one of the coefficients of a power of s is negative. Hence, the system must be designed so that the positive terms outweigh the negative terms in every coefficient. To make this polynomial more comprehensible, we normalize frequency in terms of a characteristic frequency $s_0$:

$$s_0 = SQRT(-K/M) \quad 21]$$

We may also define a characteristic damping factor $D_0$:

$$i\ D_0 = SQRT(-K*M) \quad 22]$$

Since K is negative, $s_0$ and $D_0$ are real numbers. The normalized LaPlace frequency is then defined by:

$$s' = s/s_0 \quad 23]$$

Dividing Eq. 20 by $s_0^3$ and substituting from Eqs. 21–23 yields:

$$s'^3 + s'^2((D+D_{em})/D_0 31\ 1/s_0*T_2) + s'((D_{em}/D_0)(1/s_0T_1 - 1/s_0T_2) - D/D_0s_0T_2 - 1) + 1/s_0T_2 = 0 \quad 24]$$

Eq. 24 implies no restriction on our circuit parameters. Just as, for convenience, we chose to restrict the value of $D_{em}/T_1$ in Eq. 13 to a practical value, so here we may choose to restrict the time constant $T_2$ to a "natural" magnitude, i.e. $T_2 = 1/s_0$, in which case Eq. 24 takes on a simpler appearance:

$$s'^3 + s'^2((D+D_{em})/D_0 - 1) + s'((D_{em}/D_0)(T_2/T_1 - 1) - D/D_0 - 1) + 1 = 0 \quad 25]$$

when we restrict $T_2 = 1/s_0$.

Suppose we assume (as is sometimes the case) that $D << D_{em}$ and can be neglected in Eq. 25. In that case, if we set $D_{em} = 4D_0$ and $T_1 = T_2/2$ then our characteristic polynomial becomes:

$$s'^3 + 3s'^2 + 3s' + 1 = 0 \quad 26]$$

i.e., $$(s'+1)^3 = 0 \quad 27]$$

We have three equal real poles at $s' = -1$, i.e. a system with exponential decay at the time constant $T = 1/SQRT(-K/M)$. The complete solution includes terms proportional to EXP$(-t/T)$, $t*EXP(-t/T)$, and $t^2*EXP(-t/T)$, so overshoot is possible as the second and third terms grow and decay, but there is little overshoot, no ringing, and eventual settling is driven by the exponential multiplier. This kind of response could be considered the equivalent of critical damping for a third order system.

In a configuration where the fluid damping coefficient D is significant, then the $s'^2$ coefficient grows and the $s'$ coefficient shrinks in Eq. 25. Making both $D_{em}$ and $T_1$ smaller can restore the form of Eq. 26.

One can seek faster settling by making $T_2$ smaller, renormalizing Eq. 23 to obtain unit $s'^3$ and constant coefficients, and then juggling the middle coefficients of the resulting polynomial to obtain the form of Eq. 26, or optimizing according to some criterion allowing unequal roots. There are, however, reasons to avoid faster settling. First, why bother? Second, suppose that a rotor system is designed to operate under large external acceleration forces without the rotor bumping its confining enclosure or moving very far off-center, so that good alignment between the ultrasound beam and mirror is constantly maintained. One might seek such performance on a microminiature scale, e.g., for successful operation in the wall of a beating heart. A rotor that withstands high accelerations without crashing is going to be hard to pry loose on startup. It is desired that the rotor be pried loose without such a high energy pulse that the drive coil overheats. The total pry-away energy pulse is minimized if the electric current applied never exceeds roughly 150% of the minimum threshold to pry the rotor loose. At higher peak pry-away accelerations, the square-law of $I^2R$ coil power outpaces the reduction in time to settle, leading to greater coil temperature rise. As peak pry-away force falls below 120% of the minimum threshold, the time to move the rotor to center position rises faster than the $I^2R$ power level falls, so transient coil heating again rises. The scaling of $T_2$ chosen for Eq. 25 yields about the correct speed to minimize the initializing energy pulse.

The transfer function results just derived dictate some, but not all, of the significant component values choices for the circuit of FIG. 3. In particular, the gains and time constants associated with the startup loop through OA5 are not specified. A workable set of such parameters has been obtained by computer simulation and tested successfully in an electromechanical embodiment. The following design procedures and formulas, based on the results through Eq. 27 plus computer and corroborating empirical results, are intended to lead the engineer to a practical geometric and electronic design on any chosen scale, a design that, with possible minor empirical adjustment, will initialize and maintain levitation without transient overheating or instability. Issues of external g-force and coil heating are addressed first.

Design For Adequate Restoration and Force Coupling

First, values for the Tesla-Meter coupling parameters $TM_s$ and $TM_d$ are needed for a prospective coil and magnet geometry, using textbook magnetic formulas and procedures outlined above. Achievable winding count and coil resistance $R_d$ will come from wire winding tables for larger designs, and will have to be determined from geometry and resistivity figures on a microminiature scale where metallizations and etching procedures replace conventional wire winding. Pry-away force $F_{pry}$ to free the rotor from either stop (targeting symmetry for the force from either stop) is chosen to exceed the maximum g-force (=rotor-mass-times-acceleration, including gravity) at which the rotor must maintain levitation. This force magnitude equals the magnitude of spring coefficient K, as derived from rotor/stator permanent magnet interactions, multiplied by $x_{max}$, the distance of rotor travel from center to stop position. (For typical designs, $x_{max}$ is small compared to magnet sizes and spacings, with the result that the negative restoration is comparatively linear and well-represented by a simple coefficient K.) Radial or cross-axis clearance needs to be $2*x_{max}$ for an equivalent cross-axis g-force before the rotor bumps its confining cylinder. If the magnitude of $x_{max}$ is outside an acceptable range, then one must go back to the sizing and placement of magnets, seeking a workable design. With an acceptable determination of K, $x_{max}$, and $F_{pry}$, one divides $F_{pry}$ by $TM_d$ to obtain $I_{pry}$, the pry-away drive coil current. Multiplying $I_{pry}$ by $R_d$ yields the pry-away voltage $V_{pry}$. One rechecks the emerging design for practicality of voltage and current magnitudes, adjusting as needed. Now calculate characteristic frequency $s_0$ according to Eq. 21, and characteristic damping coefficient $D_0$ according to Eq. 22.

Checking For Coil Overheating

At this point, check to be sure that the drive winding will not overheat during startup. Once the rotor is levitated, coil dissipation to maintain levitation is small, related to amplifier noise and externally-imposed vibrational acceleration that the servo must counteract. Hence, operating temperature rise is generally not a problem. Initializing temperature rise, however, can be excessive if one targets too large an $F_{pry}$ in combination with too poor a $TM_d$ coupling. For initializing temperature rise, compute characteristic energy initialization pulse magnitude $E_i=4*V_{pry}*I_{pry}/s_0$. This formula for $E_i$ is based on an initial push in the correct direction to free the rotor. If the circuitry happens to push the rotor toward its stop before reversing and pushing the rotor free, startup energy with the circuit of FIG. 3 does not exceed $5*E_i$. Compute the temperature rise by estimating the total thermal capacity of the winding copper, in degrees/joule, and multiply by $5*E_i$ in joules. If this temperature rise is a problem but the temperature rise at $1*E_i$ is acceptable, one may consider substituting a more sophisticated control system for that of FIG. 3, e.g., using a microprocessor that quickly determines failure to free the rotor for a given drive polarity (if the velocity signal doesn't change), shuts down the driver to allow the drive coil to cool (taking less than a second for a microminiature design), and restarts with the opposite polarity.

Setting Component Parameters For FIG. 3

To obtain the three equal roots of Eq. 26, we set $T_2=1/s_0$ and $D_{em}=4*D_0$, noting in the second paragraph after Eq. 27 that $T_0$ and $D_{em}$ will require adjustment if the fluid mechanical damping factor D is significant. Given a value for $D_{em}$, one sets effective loop damping resistance R to satisfy $D_{em}=K_s*K_d/R$. Given the actual drive coil resistance $R_d$, then one needs a direct voltage gain G around the loop according to $G=R_d/R$, thus raising the loop transconductance from $1/R_d$ to $1/R$. In the following, we assume that R2/R1= G, i.e. that all the direct amplification in the loop takes place at the first amplifier. With this we may choose R12=R13 and R14=R15, causing the driver built around OA4 to be a non-inverting summing amplifier with unity gain with respect to each of its two inputs.

G may turn out to be quite large, far in excess of 1000. One may need to reconsider the sense coil design and proximity to the rotor if G is impractically large. Voltage offset in OA1 may be excessive at high amplification, in which case it is acceptable to add a highpass capacitor in the topology, e.g., capacitor C6 of FIG. 3. (C6 may be omitted, as in FIG. 2, if offset is not a problem.) The time constant C6*R for R=R3-parallel-R12 should be at least $10/s_0$, which is long enough to obtain nearly the performance of a direct-coupled servo loop except for minor added overshoot. If SW1 (FIG. 3) is kept closed after power-up long enough for transient settling and passage of several time-constants of the highpass coupling capacitor, then the input offset will be "forgotten" when SW1 opens.

The lowpass pole associated with C1 and R2 should exceed $10*s_0$ in frequency, with the particular choice bounded on the high side by high-frequency stability limits associated with mutual inductance between the drive and sense coils. If that mutual inductance is large enough to force an excessively low pole frequency=1/R2C1, then compensatory high-frequency signal cancellation, e.g. coupled electrically from OA4 to OA1, may be needed to counterbalance the unwanted high-frequency loop gain.

Continuing with the OA2 integrator, set the integration time constant $R3C2=0.5/s_0$, which satisfies $T_1=T_2/2$ as expressed just before Eq. 26. If we set R6/R5=1, making OA3 a unity-gain inverter, then we obtain R7=2R3, setting $T_1$ according to the critical damping criterion first defined immediately preceding Eq. 13.

Limit voltages are scaled to $V_{pry}$, the rotor pry-away threshold described above. In the output stages of OA4, set R17 and R18 equal and such that OA4 saturates and driver output voltage limits at $1.5*V_{pry}$. With this scaling, set R5<<R3 (e.g. 5 times smaller) so that R4 is loaded much more by R3 than by the integration current set by R3 across C2. Then op amp saturation voltage is scaled down by roughly R3/(R3+R4) at the C2-R5 junction. Choose R4 to set this scaled-down saturation voltage to $3*V_{pry}$.

The components of the OA5 feedback loop are determined interactively, depending particularly on a convenient voltage threshold $V_z$ for the back-to-back ZD1 and ZD2 combination. Going around the 3-amplifier loop, one has two integration time-constants, R11C2 and R4C3. Setting the time constant product according to $R11C2R4C3=0.6/s_0^2$ gives a good setting for overall performance. Compare this op amp topology to a state-variable oscillator circuit, with the zener diodes introducing a deadband such that the oscillator loop is opened whenever the servo loop through the rotor is closed and stable. The choice for R11C2R4C3 leads to a state variable oscillator frequency of $s_0$/SQRT (0.6). The deadband threshold in the loop slows things down so that the oscillation frequency of the loop works out to about $s_0$, an effective magnitude for prying the rotor loose but not continuing to push in the same direction for too long, so that the rotor can be stopped and controlled in its free range. With these settings, the damping resistor R9 is set in relation to C3 to give a pole time constant $C3R9=7/s_0$. This setting determines the net damping around what resembles a state variable oscillator loop. If C3R9 is too small, the loop is not strongly enough regenerative and DC latchup occurs. If C3R9 is too large, then the OA5 circuit continues to swing outside the deadband thresholds when the rotor flies, resulting in sustained blocking oscillations.

Given net $V_z$ for series diodes ZD1 and ZD2, then set $R11/R3=0.15*V_z/V_{pry}$. This scales the current in R11 relative to R3 in the same proportion as $V_z$ in relation to $V_{pry}$, which permits flexibility in the choice of $V_z$. For many zener diodes, leakage current is large enough in relation to the current magnitude that typically flows through R11 that one needs a grounded load resistor, R10, of magnitude well below R11, to absorb the leakage and obtain good zener threshold performance. One can alternatively scale for use of parallel oppositely-directed diodes in place of the series zeners, using the forward voltage threshold at a current magnitude set by R11 or R10. Finally one must choose C2 and C3 values, which will result in determination of all the resistor values. It is convenient and practical to set C2=C3. If there is an AC coupling capacitor from OA1, one typically sets this to the largest convenient magnitude for a non-electrolytic capacitor, e.g., 1 microfarad. The AC coupling time constant prescription then scales R3, which in turn sets C2. Setting C3=C2 finally leads to values for all the remaining components by the ratio guidelines given above.

DESIGN FOR DRIVING ROTATION

Once a rotor is levitated, obtaining rotation is a relatively easy matter. The designer is cautioned that on a microminiature scale, the rotation of a rotor immersed in fluid (e.g., water) is damped more than intuition might indicate. For example, for a rotor of uniform diameter of 0.020 inches inside a 0.023 inch inside-diameter cylinder, a rotor spinning at 3000 RPM will be nearly stopped, upon removal of torque, in less than a revolution. Keeping a small rotor spinning steadily therefore requires a continuous application of electromagnetic torque. Hence, it is difficult to maintain a comparatively constant rotation speed on a very small scale using a single-phase rotation drive signal.

Figure 4:
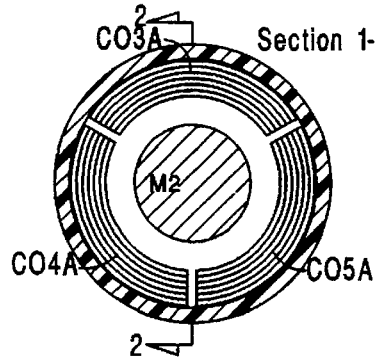
FIG. 4 is a cross-sectional view of the drive coil arrangement for a three-coil, three-phase rotation drive.

A good drive coil geometry for a high torque$^2$/watts ratio is three coils arrayed on 120-degree centers around the cross-axis magnet, driven by a three-phase sinusoidal oscillator output. When two pairs of opposing coils are used for a two-phase drive (with 90° relative phases), one has four coils instead of three, which provides less space for the coil conductors and less "wrap-around" of the coils to couple a cross-axis field across the center of the rotor, generally resulting in a lower achievable torque$^2$/watts figure. FIGS. 3 and 4 show, in two section planes, the placement of three rotation-drive coils with 120-degree symmetry about the center of M3, the cross-axis magnet. The geometry of each coil could be described as an initially rectangular coil placed on the inner surface of cylindrical window USW and then bent along opposite sides A and B so that these two sides conform to the inner window surface, taking a circumferential path, while the remaining two sides joining sides A and B are aligned axially, following the inner surface of USW. FIG. 3 is Section 2—2 of FIG. 4 while FIG. 4 is Section 1—1 of FIG. 3. The section of FIG. 3 cuts across sides A and B of coil 3, indicated by "CO3A" and "CO3B" above magnet M2, while an axial side of coil 4 lies just behind Section 2—2 and is indicated by its ends at "CO4A" and "CO4B" where the ends of the axial segment meet the curved sides A and B. The three curving sides of coils 3, 4, and 5 at end A are indicated in FIG. 4 by "CO3A", "CO4A", and "CO5A".

As is known in motor practice, a three-phase electrical drive can be applied via three drive conductors, either with each drive conductor joined to two of the six coil connecting wires, or with each drive conductor joined to just one of the six coil connecting wires while the remaining three coil connecting wires join together at a "common" junction that does not require connection to a common grounding wire.

Either a two- or three-phase electrical drive generates a continuously rotating cross-axis magnetic field vector that defines a "preferred" rotational alignment for the rotor at each instant. Actual rotational alignment will lag at some angle behind this "preferred" alignment, depending on friction. This rotation lag angle can be estimated in self-calibrating fashion, or measured via back-EMF, or measured via a "marker" on the ultrasound window that is visible in the displayed image. The self-calibrating approach determines a combined rotation drive-current amplitude and frequency threshold where friction just exceeds available torque and causes the rotor to fall out of synch and quit spinning, as evidenced, e.g., by the abrupt appearance of bilateral symmetry in the polar-coordinate ultrasound image (as the ultrasound beam actually swings back and forth across an angular sector rather than completing full rotations.) This loss-of-synch threshold indicates relative friction magnitude, which in turn predicts angle lag for drive currents and frequencies where synch is maintained. The back-EMF measurement approach pulses the rotation drive currents and measures the induced back-EMF in one or more drive conductors during the current-off intervals. The pulsing can be at many pulses per revolution, or using two broad on-pulses per wire per phase, for the positive and negative output swings on that wire, with short off-intervals to measure back-EMF in the transitions from positive-to-negative and negative-to-positive drive currents. The back-EMF signal is proportional, at each instant, to the product of angular velocity times the sine of the geometric angle between rotor alignment and an alignment of the coil or coils associated with the given drive conductor. In instances where accurate determination of absolute angle reference is unimportant, or where a standard drive current level, rotation rate, and probe temperature (e.g. body temperature) lead to a fairy reproducible angle lag, a typical lag angle can be determined once, e.g., using a phantom, and employed in the calibration of subsequent manufactured ultrasound systems.

While other approaches are available for measuring the axial position of a levitated ultrasound-reflecting rotor in order to achieve bearingless rotation, the above specification details a preferred approach with extremely simple design requirements for the rotor and with characteristics appropriate for microminiature scale. A broader sense of the invention is conveyed by the following claims which include equivalents of the invention described herein.

I claim:

1. An ultrasonic imaging device comprising:
   a. a housing having a region transparent to ultrasonic signals;
   b. a mirror within said housing and obliquely aligned with an ultrasonic transducer, wherein said mirror is designed to reflect ultrasonic signals transmitted by said transducer; and
   c. a device for rotating and suspending said mirror including a rotor coupled to said mirror, wherein said rotor and said mirror are suspended and rotated without mechanical bearings within an ultrasonically conductive fluid within said housing.

2. The device as claimed in claim 1 further comprising an electronic controller for detecting and controlling the operation of said rotor.

3. An ultrasonic imaging device comprising:
   a. a housing having a region transparent to ultrasonic signals;
   b. a mirror within said housing and obliquely aligned with an ultrasonic transducer, wherein said mirror is designed to reflect ultrasonic signals transmitted by said transducer;
   c. a rotor comprising a first magnetic region, a second magnetic region, and a third magnetic region, wherein said first magnetic region is connected to said mirror; and
   d. stator means comprising a first stator block connected to said housing proximal to said rotor, and a second stator block connected to said housing distal to said rotor,
   wherein said first magnetic region and said third magnetic region have oppositely-directed dipole moments substantially axially aligned with said rotor, wherein said second magnetic region lies between said first magnetic region and said third magnetic region and has a dipole moment substantially transversely aligned with said rotor, and wherein said first stator block and said second stator block have oppositely-directed dipole moments substantially axially aligned with said rotor.

4. The device as claimed in claim 3 further comprising active means for axially positioning said rotor within said housing.

5. The device as claimed in claim 4 wherein said active means for axially positioning said mirror includes one or more position coils coaxial with said first stator block and said second stator block, wherein said one or more position coils in conjunction with said magnetic regions of said rotor push or pull said rotor into a determined axial position within said housing.

6. The device as claimed in claim 5 wherein said determined axial position is adjusted over time to minimize power to said one or more position coils.

7. The device as claimed in claim 5 further comprising means to detect the axial velocity of said rotor within said housing, said means to detect the axial velocity including one or more sense coils coaxial with said first stator block and said second stator block.

8. The device as claimed in claim 7 further comprising servo means coupling said one or more position coils with said one or more sense coils such that a sensed velocity of said rotor may be used to control the operation of said one or more position coils.

9. The device as claimed in claim 8 wherein said servo means includes an electronic feedback circuit.

10. The device as claimed in claim 9 wherein one of said one or more position coils may operate as one of said one or more sense coils.

11. The device as claimed in claim 3 wherein said device for rotating and suspending said mirror includes one or more field coils for changing a cross-axis magnetic field applied to said rotor, wherein said one or more field coils are cross-axial with said first stator block and said second stator block.

12. An ultrasonic imaging method comprising the steps of:
   a. connecting an ultrasonically-reflective mirror to a rotor;
   b. magnetically suspending said rotor within an ultrasonically conductive fluid; and
   c. rotating said mirror and said rotor within said ultrasonically conductive fluid.

13. The method as claimed in claim 12 further comprising the step of axially positioning said mirror and said rotor within a housing containing said mirror and said rotor.

14. The method as claimed in claim 13 wherein said rotor includes magnetic regions and the step of positioning said mirror and said rotor within said housing includes axially positioning said rotor by applying a changing axial magnetic field gradient to said magnetic regions of said rotor.

15. The method as claimed in claim 14 wherein the step of applying a changing axial magnetic field gradient field includes connecting one or more position coils to said housing.

16. The method as claimed in claim 15 wherein the step of positioning said mirror and said rotor within said housing includes creating in said rotor a first magnetic region and a third magnetic region having oppositely-directed dipole moments axially aligned with the orientation of said rotor, and a second magnetic region having a dipole moment transversely aligned with the orientation of said rotor, wherein said second magnetic region lies between said first magnetic region to said third magnetic region.

17. The method as claimed in claim 15 further comprising the step of coupling said one or more position coils to means for controlling the operation of said one or more position coils.

18. The method as claimed in claim 17 further comprising the step of coupling said means for controlling the operation of said one or more position coils with one or more sense coils.

19. The method as claimed in claim 18 further comprising the step of generating a transfer function amplification between said one or more position coils and said one or more sense coils.

20. The method as claimed in claim 19 wherein said transfer function amplification includes signal gain summed with signal integration, wherein said signal integration is modifiable by regenerative feedback.

21. A levitation position control system comprising:
 a. a driver coupled to and for positioning an object;
 b. sense means for generating a velocity signal from movement of said object;
 c. integration means for converting said velocity signal into a position signal;
 d. velocity servo means for employing said velocity signal and said position signal to generate a drive signal that servoes said position signal to a target value; and
 e. integration offset correction means for causing said drive signal progressively to re-bias said position signal.

22. The system as claimed in claim 21 wherein said object includes a magnetic rotor and said driver includes position coils for exerting a force on said magnetic rotor.

23. The system as claimed in claim 22 wherein said sense means includes one or more sense coils coaxial with said magnetic rotor.

24. The system as claimed in claim 23 wherein said velocity servo means includes an electronic feedback circuit between said sense coils and said driver.

25. A method for controlling the levitation position of an object, said method comprising the steps of:
 a. exerting a driving force to said object;
 b. generating a velocity signal indicating a change in a position of said object;
 c. integrating said velocity signal to obtain a position-indicating signal;
 d. determining said driving force as a function of said velocity signal and said position-indicating signal, such that said position-indicating signal approaches an equilibrium value; and
 e. progressively correcting an offset of said position-indicating signal in response to said driving force.

26. The method as claimed in claim 25 wherein the step of progressively correcting said offset minimizes the magnitude of said driving force.

* * * * *